United States Patent [19]

Poklacki

[11] 3,969,253
[45] July 13, 1976

[54] METHOD FOR LOWERING THE MINIMUM POUR TEMPERATURE OF FATTY ACIDS

[75] Inventor: Erwin S. Poklacki, Arlington Heights, Ill.

[73] Assignee: Borg-Warner Corporation, Chicago, Ill.

[22] Filed: Jan. 2, 1974

[21] Appl. No.: 430,294

[52] U.S. Cl. .............................. 252/77; 252/363.5; 252/364; 252/DIG. 14; 252/DIG. 13; 252/DIG. 16; 252/89 R; 252/117; 260/283 R; 260/283 P; 44/66; 44/72; 424/325; 424/168; 424/172
[51] Int. Cl.² ........................................ C09K 50/06
[58] Field of Search .................. 252/77, 363.5, 364; 260/283 R, 283 P

[56] References Cited
UNITED STATES PATENTS

| 2,053,853 | 9/1936 | Van Peski | 252/77 X |
| 3,285,718 | 11/1966 | Whitfield et al. | 44/7 |
| 3,290,307 | 12/1966 | Keller et al. | 260/249.6 |
| 3,373,107 | 3/1968 | Rice et al. | 260/583 R |
| 3,726,926 | 4/1973 | Brown et al. | 260/583 R X |
| 3,846,481 | 11/1974 | Gaydasch | 252/77 X |

FOREIGN PATENTS OR APPLICATIONS

| 569,600 | 1/1959 | Canada | 252/77 |
| 1,444,838 | 5/1970 | Germany | 252/77 |

Primary Examiner—Marion E. McCamish
Assistant Examiner—Patricia C. Ives
Attorney, Agent, or Firm—Richard J. Schlott

[57] ABSTRACT

The minimum pour temperature of a fatty acid, analogous to the ASTM pour point of a hydrocarbon oil, may be lowered by 70°F. and more by the method of this invention, which comprises mixing therewith from 5 to about 50 parts by weight of a $C_2$–$C_{18}$ acyclic monoamine or diamine. The method of this invention is applicable to a wide variety of fatty acids and mixtures.

5 Claims, No Drawings

METHOD FOR LOWERING THE MINIMUM POUR TEMPERATURE OF FATTY ACIDS

BACKGROUND

Fatty acids are a class of carboxylic acids characterized as the saturated and unsaturated long chain acids commonly derived from natural fats and waxes. When obtained from natural sources, the compositions are generally mixtures containing varying amounts of individual fatty acid compounds and numerous minor components. Modern synthetic methods permit the manufacture of many of the natural compounds and their analogs, either as nearly pure single substances or as mixtures. For purposes of this application, the term fatty acid is intended to be inclusive of both natural and synthetic compounds, singly and in mixtures.

Fatty acids are widely used in the preparation of soaps, detergents, cosmetics and in certain formulations for gelling liquid hydrocarbon fuels. Manufacturing processes for many of the products often require that large volumes of fatty acids be transferred, and when the fatty acid is liquid at the ambient temperature or can be melted at a convenient temperature the transfer method of choice is pumping through tubing to the point of use. In formulations for the gelling of liquid hydrocarbons, transport of the fatty acid and rapid mixing to form solutions in the liquid hydrocarbon are made more practical when the fatty acid is liquid. Many of these gelling applications are intended to be used as continuous processes or in situations where the object is an extremely rapid gel formulation, and pumpability and fast mixing are prerequisites. One example of such an application is the use of fatty acids together with a caustic to gel and solidify aircraft fuel under emergency conditions, where the dispersion and dissolving of the fatty acid must occur extremely fast in order to be of any practical benefit. In these and similar gel-forming or thickening applications, the preferred fatty acids are liquid at the temperature ambient to the use, which confers the benefit of extremely rapid transfer and fast solubility.

Of the fatty acids readily available commercially, relatively few are liquid at the normal room temperature condition, and the number exhibiting pourability at the lower outdoor temperatures commonly encountered in a temperate climate are very few. Additionally, many of the natural sources of fatty acids have become increasingly limited in supply, and replacements have had to be found for many widely used commercial compositions such as the tall oils and the oleic acid mixtures, both of which are pourable liquids at relatively low temperatures. Recourse to synthetic sources has been less than satisfactory since very few synthetic mixtures exhibit pourability at usefully low temperatures.

Accordingly, a method for lowering the minimum pouring temperature of fatty acids would permit the use of a wider number of the available fatty acids in applications where pourability is a necessary and desirable characteristic. Additionally, in manufacturing processes employing fatty acids as starting materials, improving the pourability of the particular fatty acids employed could permit transfer under the ambient condition by pumping, thereby potentially improving process economics and in some instances effecting a saving in heat energy requirements.

SUMMARY

It has now been found that the addition of small amounts of amines to fatty acids and fatty acid mixtures results in compositions having surprisingly improved pourability. More particularly, it has been found that fatty acid compositions comprising as little as 5 parts of an amine per hundred parts of fatty acids exhibit minimum pourability temperature values as much as 20°F. below that of the fatty acid alone.

DETAILED DESCRIPTION

The amino compounds useful in the practice of this invention are selected from the group characterized as acyclic monoamines and diamines. The acyclic monoamines are represented by the formula

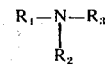

wherein $R_1$, $R_2$ and $R_3$ are independently selected from the group H and $C_1-C_6$ lower alkyl with the limitation that the total number of carbon atoms in the structure must be in the range 2 to 18. The acyclic diamines are represented by the structure

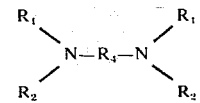

wherein $R_1$ and $R_2$ have the meaning given hereinabove and $R_4$ is $C_1-C_6$ alkylene, with the limitation that the total number of carbon atoms in the structure must be in the range 2 to 18.

The fatty acids for which the practice of this invention provides a useful lowering of minimum pouring temperature are virtually all the fatty acids as well as mixtures containing fatty acids in substantial proportion. That is, it has been found that substantial lowering of the minimum pouring temperature occurs for fatty acids, such as lauric acid, which alone are solid waxes at ordinary room temperatures. Similarly, fatty acid mixtures such as tall oil, liquid at room temperature and solidifying at temperatures near 0°F., remain pourable to significantly lower temperatures when mixed with the amines disclosed herein.

The concentration in which the amines may be employed may vary between wide limits depending upon the particular amine selected, the pouring temperature characteristics of the fatty acid, and the degree of improvement envisioned. In some instances, as little as 5 parts by weight of amino compound per hundred parts by weight of fatty acid will produce the effect desired. In other cases, where the effect desired is one of a large decrease in minimum pour temperature, as much as 50 parts by weight per hundred parts of fatty acid may be necessary. Inasmuch as the primary goal of the invention is to provide fatty acids with lowered minimum pour temperatures, it will be recognized that compositions containing a major or even substantial proportion of an amine will be of limited utility for some end uses. Hence, it is preferred that the level of amine not exceed 50 parts by weight, and more preferably not more than 25 parts by weight per hundred parts of fatty acid.

The effectiveness of the various amines included in the scope of this invention will vary. Those preferred for the practice of this invention generally impart a decrease of at least 10°F. in the minimum pour temperature at a concentration of 10 parts by weight per hundred parts of fatty acid. It should be understood that these effects are markedly greater than normally result from the addition of small amounts of mere solvents. Inert solvents, such as hydrocarbons, generally impart a rather minor lowering of minimum pour temperature. The increment of decrease produced by solvents is rather closely a direct function of concentration and the pour temperature is therefore linearly reduced in proportion to solvent concentration. The amines useful for the purposes of the invention produce very large effects, and the minimum pour temperatures are reduced in a non-linear and unpredictable fashion.

Minimum pour temperature is the lowest temperature at which the material in test will flow when cooled without disturbance at a fixed rate. The determination of minimum pour temperature is made by an adaptation of a standard test for determining pour point of petroleum oils, published as ASTM test D-97-66. The test as used for the determination minimum pour temperatures of fatty acids was carried out as follows:

A sample of the fatty acid was weighed into a standard test jar and warmed until completely molten. A weighed amount of the amine was then added and mixed thoroughly. The test jar was placed into a standard test apparatus and the sample was cooled. The pourability of the mixture was observed every 5°F. until solidification was observed. The solidification point was recorded as the temperature at which no movement of the material occurs when the sample jar is held horizontal for 5 minutes. The minimum pour temperature is recorded as 5°F. above the solidification point.

The effectiveness of the particular method of this invention in lowering the minimum pour temperature of fatty acids will be further elucidated by way of the following examples.

EXAMPLE 1

Triethylamine as a pour temperature depressant

Triethylamine was mixed at several levels with a fatty acid mixture containing largely $C_{16}$–$C_{18}$ fatty acids sold by General Mills Chemicals, Inc. under the designation Alophat 47E. The mixtures were prepared by heating the fatty acid to melting, mixing thoroughly with the indicated amount of triethylamine, then cooling and obtaining the minimum pour temperature of the mixture by the test procedure outlined hereinabove. The results are reported in Table I, where all parts are by weight.

Table I.

| Example No. | Pour Temperature Lowering with Triethylamine | | | | | | |
|---|---|---|---|---|---|---|---|
| | 1A | 1B | 1C | 1D | 1E | 1F | 1G |
| Triethylamine, parts | 0 | 5 | 10 | 15 | 20 | 29 | 50 |
| Alophat 47E, parts | 100 | 100 | 100 | 100 | 100 | 100 | 100 |
| Pour Point, °F. | 75° | 65° | 35° (40°) | 30° | 25° | 15° | 10° |

It will be apparent from these data that compositions containing relatively small amounts of triethylamine have very markedly lowered minimum pour temperatures. Further, it will be noted that the effect is surprisingly non-linear, large effects occuring at the low levels (Experiments 1A–1D) and further increases in amine concentration (Examples 1E –1G) producing smaller additional decreases in pour point temperature.

EXAMPLES 2–8

Comparison Tests with Solvents

The tests described in Example 1 for triethylamine were repeated with several solvents. These results are tabulated in Table II.

Table II.

| Example No. | Solvents in Pour Point Temperature Lowering for Fatty Acids | | |
|---|---|---|---|
| | Fatty Acid(1) 100 Parts by wt. | Additive ( ) Parts by wt. | Pour Point °F |
| — | Alophat 47E | Control | 75° |
| 2A | Alophat 47E | Xylene (15) | 60° |
| 2B | Alophat 47E | Xylene (30) | 50° |
| — | Alophat 34W | Control | 100° |
| 3A | Alophat 34W | Toluene (50) | 80° |
| 3B | Alophat 34W | Toluene (100) | 70° |
| 4A | Alophat 34W | Xylene (25) | 85° |
| 4B | Alophat 34W | Xylene (50) | 80° |
| 4C | Alophat 34W | Xylene (100) | 70° |
| 5 | Alophat 34W | Diesel Fuel (58) | 85° |
| 6 | Alophat 34W | Hexane (50) | 75° |
| 7A | Alophat 34W | Parafin Oil (50) | 90° |
| 7B | Alophat 34W | Parafin Oil (100) | 85° |
| — | LD 21271 | Control | 70° |
| 8A | LD 21271 | Xylene (8) | 70° |
| 8B | LD 21271 | Xylene (28) | 65° |

Notes: (1)
Alophat 34W, commercial fatty acid mixture, General Mills Chemicals, Inc., containing $C_{16}$-$C_{18}$ fatty acids derived from soybean oil.
Alophat 47E, commercial fatty acid mixture, General Mills Chemicals, Inc., containing largely $C_{16}$-$C_{18}$ fatty acids.
LD 21271, fatty acid mixture, isolated from Tall Oil, Enjay Chemical Co.

When compared with the data for Example 1, it becomes immediately apparent that the effect of amines in lowering pour point temperatures of fatty acids is far greater than is found for inert solvents. The effect of an inert solvent is both small and fairly consistently a direct function of concentration. As shown for example by Example 2B, wherein 30 parts of xylene produce a smaller effect than 10 parts of triethylamine (Example 1C).

EXAMPLES 9–14

Comparison of Amines in Pour Temperature Lowering

A variety of amino compounds were compared for their ability to lower the pour temperature of the commercial fatty acid Alophat 47E, as in Example 1. These data are collected in Table III.

Table III.

| | Effectiveness of Various Amino Compounds in Minimum Pour Temperatures | | | |
|---|---|---|---|---|
| Example No. | Amine | Minimum | Pour | Temperature (F) |
| | | 0 parts* | 5 parts* | 10 parts* | 30* parts |
| 9 | Trimethylamine | 75 | 55 | 45 | |
| 10 | Diethylamine | 75 | 60 | 30 | |
| 11 | Tri-n-propylamine | 75 | 70 | 60 | 10 |
| 12 | Octylamine | 75 | 65 | 55 | |
| 13 | Di-isopentylamine | 75 | 65 | 60 | −5 |
| 14 | N,N,N′,N′-Tetramethylethylenediamine | 75 | 55 | 50 | |
| 15 | Trioctylamine | 75 | 70 | 70 | |
| 16 | Triethylenetetramine | 75 | 70 | 85 | |
| 17 | Triethanolamine | 75 | 70 | 70 | |
| 18 | N,N dimethylaniline | 75 | 65 | 65 | |
| 19 | Pyridine | 75 | 70 | 70 | |
| 20 | Piperazine | 75 | 75 | —(1) | |
| 21 | Dimethylformamide | 75 | 70 | 65 | |
| 22 | Urea | 75 | 70(75) | —(2) | |
| 23 | Primine JM-T(3) | 75 | 70 | 70 | |
| 24 | Priminox RJM(3) | 75 | 70 | 70 | |

Notes:
(1)Mixture became gelatinous
(2)not soluble
(3)commercial amine additives for lube oils. Primine JM-T:isobutylene Trimer amine; Priminox RJM:ethoxylated isobutylene Trimer amine (Rohm and Haas).
*Parts by weight amine per 100 parts Alophat 47E.

As will be apparent from examples 9–14, simple low molecular weight acyclic amines and diamines are quite effective in lowering pour temperature of fatty acids, while higher molecular weight amines, polyamines (Example 16) hydroxylic amines (Example 17) and aromatic amines (Examples 18 and 19) give little or no lowering of pour temperature. Similarly, amides (Examples 21–22) are also ineffective, as are commercial amine based lube oil additives (Examples 23–24). It will also be noted that the various amines differ slightly in behavior at low concentration, that is some produce a minimal change at 5 parts per hundred and sharply depress the pour temperature at 10 parts per hundred (Examples 1, 12), others produce a large effect even at 5 parts per hundred (Examples 9, 10, 14) and still others give a minimal effect at 10 parts per hundred but produce large decreases at 30 parts per hundred. As has been said before, the object of the invention is to provide fatty acids with reduced minimum pour temperatures, and as a practical matter it is not normally desirable to include large amounts of a secondary material in most fatty acid applications. Hence, the compounds regarded as useful for the purpose of this invention will produce sharp decreases in pour temperature below a concentration of 50 parts per hundred, preferably below about 25 parts per hundred of fatty acid.

EXAMPLES 25–33

Effect of Triethylamine on the Minimum Pour Temperature of Various Fatty Acids

The procedure to Example 1 was followed to demonstrate the applicability of the method to a variety of fatty acids, and mixtures. These data are collected in Table IV.

Table IV.

| | Effect of Triethylamine at Various Levels on Minimum Pour Temperatures of Fatty Acids | | | |
|---|---|---|---|---|
| Example No. | Fatty Acid 100 parts | Minimum | Pour | Temperature (°F) |
| | | 0 parts* | 5 parts* | 10 parts* | 15 parts* |
| 25 | Stearic Acid | 155 | 150 | 130 | 115 |
| 26 | Lauric Acid | 115 | 110 | 90 | 50 |
| 27 | Alophat 34W | 100 | 95 | 75 | 60 |
| 28 | Tallow Acids | 100 | 95 | 70 | 60 |
| 1 | Alophat 47E | 75 | 65 | 35(40) | 30 |
| 29 | Soya Acids | 75 | 70 | 50 | 35 |
| 30 | LD 31271 | 70 | 60 | 30 | 25 |
| 31 | Linseed Oil acids | 60 | 55 | 30 | 20 |
| 32 | Oleic Acid | 30 | 25 | −5 | −15 |
| 33 | Tall Oil | 5 | −15 | −25 | — |

Notes:
*Parts by weight Triethylamine per 100 parts Fatty Acid.

As with the data of Example 1, these data demonstrate that large changes in pour temperature result with the addition of small amounts of triethylamine, whether the composition is based on a higher melting simple fatty acid (Example 26) or low melting, single fatty acid (Example 32) or complex fatty acid mixtures (Example 33). Further, in most instances the effect with small amounts of amine is very much greater than that which can be produced with even large amounts of solvents, as shown by comparing the data of Table II with the data of Table IV.

EXAMPLE NO. 34

The method of this invention can also be practiced in the presence of solvents and inert diluents. In a separate experiment, 100 parts of Alophat 34W fatty acid having a minimum pour temperature of 100°F. when admixed with 50 parts by weight of xylene as described hereinabove had a minimum pour temperature of 80°F., and when further admixed with 15 parts by weight triethyl amine then had a minimum pour temperature of 25°F.

The instant invention, then, is a useful method for lowering the minimum pour temperature of fatty acids by incorporating acyclic amines. The resulting fatty acid amine mixtures remain liquid at temperatures significantly lower than the fatty acid alone, and are thus fully useful in most fatty acid applications where the physical characteristics of a liquid are necessary or desired.

The practice of the method of this invention has been demonstrated by way of examples, which have been provided for the purposes of illustration and not by way of limitation. Variations including, but not limited to, the use of mixed amines, the concurrent incorporation of inert solvents, and the use of the method in connection with mixtures of fatty acids with other materials will be apparent to those skilled in the art, and the scope of the invention should be given the broadest interpretation consistant with the appended claims.

We claim:

1. A fatty acid composition having a lowered minimum pour temperature consisting essentially of a fatty acid and from 5 to 50 parts per hundred parts of fatty acid of at least one 2 to 18 carbon atom acyclic amine having the structure $R_1R_2R_3N$ wherein $R_1$, $R_2$ and $R_3$ are independently selected from the group H and $C_1$–$C_6$ lower alkyl.

2. The fatty acid composition of claim 1 further comprising from 5 to about 100 parts by weight per hundred parts of the fatty acid of an inert hydrocarbon diluent for the fatty acid.

3. A method for lowering the minimum pour temperature of fatty acids comprising mixing therewith from 5 to 50 parts by weight per hundred parts of fatty acid of at least one 2 to 18 carbon atom acyclic amine selected from the group consisting of $R_1R_2R_3N$ and $R_1R_2NR_4NR_1R_2$ wherein $R_1$, $R_2$ and $R_3$ are independently selected from the group H and $C_1$–$C_6$ lower alkyl and $R_4$ is a $C_1$–$C_6$ alkalene radical.

4. The method of claim 3 wherein the acyclic amine has the structure $R_1R_2R_3N$ and wherein $R_1,R_2$ and $R_3$ are independently selected from the group H, methyl, ethyl, propyl and butyl.

5. The method of claim 3 wherein the acyclic amine is selected from the group trimethylamine, triethylamine, tripropylamine, N,N,N',N' tetraethylene diamine, diethylamine, di-isopentylamine, and octylamine.

* * * * *